United States Patent [19]

Höök et al.

[11] Patent Number: 4,784,989

[45] Date of Patent: Nov. 15, 1988

[54] MEANS FOR REMOVING MICROORGANISMS FROM TISSUE

[76] Inventors: Magnus Höök, 478 Malma Ringväg, S-752 40 Uppsala; Torkel Wadstroöm, P.O. Box 96, S-741 00 Knivsta, both of Sweden

[21] Appl. No.: 611,000

[22] PCT Filed: Sep. 13, 1983

[86] PCT No.: PCT/SE83/00323

§ 371 Date: May 14, 1984

§ 102(e) Date: May 14, 1984

[87] PCT Pub. No.: WO84/01108

PCT Pub. Date: Mar. 29, 1984

[30] Foreign Application Priority Data

Sep. 14, 1982 [SE] Sweden .................. 8205244

[51] Int. Cl.[4] .................. A61K 37/02; A61K 9/70
[52] U.S. Cl. .................. 514/21; 514/2; 424/431; 424/446; 424/447
[58] Field of Search .................. 424/101, 27, 101, 431, 424/446, 447; 514/2, 21

[56] References Cited

U.S. PATENT DOCUMENTS

| | | | |
|---|---|---|---|
| 4,225,580 | 9/1980 | Rothman et al. | 424/78 |
| 4,427,650 | 1/1984 | Stroetmann | 424/101 |
| 4,427,651 | 1/1984 | Stroetmann | 424/101 |
| 4,453,939 | 7/1984 | Zimmerman et al. | 424/177 |
| 4,478,829 | 10/1984 | Lawdaburu et al. | 424/101 |

FOREIGN PATENT DOCUMENTS

| | | |
|---|---|---|
| 0058993 | 1/1982 | European Pat. Off. . |
| 1602339 | 5/1978 | United Kingdom . |
| 1602340 | 5/1978 | United Kingdom . |
| 2041377 | 1/1980 | United Kingdom . |

OTHER PUBLICATIONS

Chemical Abstracts 66:44064r (1967).
Chemical Abstracts 74:30657q (1971).
Chemical Abstracts 102:60148p (1985).
Espersen, F. et al, "Isolation of a Fibronectin-Binding Protein from *Staphylococcus aureus*," *Infection and Immunity*, vol. 37, No. 2, pp. 526–531 (1982).

*Primary Examiner*—Jerome D. Goldberg
*Attorney, Agent, or Firm*—Burns, Doane, Swecker & Mathis

[57] ABSTRACT

This invention relates to a method for treating microorganism infection on wounds by applying to the microorganisms on the wounds an effective amount or a protein or fragment or residue selected from the group consisting of fibronectin, fibrinogen, collagen, laminin and chondronectin the protein of fragment or residue thereof.

10 Claims, No Drawings

MEANS FOR REMOVING MICROORGANISMS FROM TISSUE

The present invention concerns means for removing microorganisms from tissue, such as mucous membranes, skin and wound tissue.

On skin and mucous membranes there is an indigenous flora of non-pathogenic as well as potentially pathogenic microorganisms. The presence of the indigenous flora serves certain useful functions and can prevent colorization of pathogenic microorganisms. Someone who in this way carries pathogenic microorganisms is a potential carrier of pathogens as the pathogenic microorganisms from such a person can be transferred to a tissue wound.

With the expression microorganisms is meant Gram-positive bacteria, such as different species of staphylococci, streptococci and pneumococci, Gram-positive rods, such as mycobacteria, e.g. *Mycobacterium leprae*, Gram-negative bacteria, such as different species of the family Enterobacteriaceae, e.g. *Escherichia coli*, Klebsiella, Proteus, Enterobacter or Vibrionacae, or Pseudomonas, as well as Gram-negative cocci, such as gonococci. This expression also includes anaerobic bacteria, such as Bacteroides, fusobacteria, anaerobic cocci, e.g. peptococci and peptostreptococci, as well as spirillae and spirochetes. Further included are fungi, such as Candida, e.g. Candida albicans, and dermatophytes, as well as pathogenic amoebae, such as *Entamoeba histolytica*, and *Giardia lamblia* and *Leishmania*.

The ways of removing microorganisms from tissue vary due to type of tissue and microorganism, respectively. For removing pathogenic microorganisms from mucous membranes and skin tissue a disinfectant or antibiotic is often used. A drawback with this is that the indigenous flora is removed as well, and thus the functions it serves. Further drawbacks are that disinfectants are cell toxic and that today many pathogenic strains have developed resistance against a large number of antibiotics. The removal of pathogenic microorganisms from wound tissue is carried out in several ways. One way is a direct attack on the microorganisms by treatment with disinfectants or antibiotics, but this is inefficient and results in the above mentioned drawbacks the indigenous flora. Another way is mechanical cleaning of wound tissue by means of moist saline dressings. The drawbacks with this are i.a. that the tissue healing is inhibited and that such dressings must be changed very often. The latter is an example of a more indirect way of removing pathogenic microorganisms from wound tissue. The secretions from the wound tissue are excellent substrate for microorganisms, and by reducing the amount thereof the growth of the microorganisms will also be decreased. Other methods wherein this indirect way is used are treatment of wounds by means of suitable polymers, e.g. in particle form, which polymers absorb the secretions from the wound tissue. Some of these secretion-absorbing polymers contain complexly bound iodine (so called iodophores), and with these a secretion-absorption and a disinfection are simultaneously achieved.

The present invention concerns means for removing microorganisms from tissue without influencing the indigenous flora in any greater extent.

A predominant cause of primary wound infections and postsurgical infections are certain Gram-positive cocci, such as *Staphylococcus aureus* and so called β-hemolysing streptococci from group A, C and G. *Pathogenic staphylococci* exist everywhere in the environment, also that of a hospital where up to 80% of the personnel can be carriers of pathogens. Yellow staphylococci (*S. aureus*) colonize especially in certain parts of the skin, such as the axilla, the bottom of the pelvis and on the hand as well as in the nose. Even in dry eczema there is a frequent existence of white as well as yellow staphylococci. The common tonsillitis bacteria *Strepococcus pyogenes* (group A streptococcus) exists in a high frequency on nursing personnel as well as patients. Nosocomial infections are often transferred exogenic (from e.g. personnel to a patient) or endogenic (patients having these microorganisms on skin or mucous membranes infect their own wounds) and this has become an increasing problem. In order to decrease the frequency of these infections classical preventive steps have so far been taken, such as careful pre-surgical cleaning and bandaging of infected eczema in separate rooms.

The first step in most infection processes is the binding of the microorganism to tissue. The microorganisms bind specifically, either direct to a component on the surface of the epithelium cell or to extracellular molecules in blood clot or in connective tissue being exposed to the microorganisms in an epithelium wound.

The present invention is based upon a completely new principle for removing microorganisms from tissue, which principle is based upon inhibition of the binding of the microorganisms to the tissue proteins on mucous membranes, skin and in wounds.

Pathogenic staphylococci have on their cell surface a protein (protein A) that specifically binds to the complement binding site (Fc-site) of immunoglobulins of different classes in a great number of animal species. This binding specificity is used in immunological tests and for removal of antibodies in extracorporal circulation by means of protein A bound to a solid phase.

It is also known that staphylococci are agglutinated by normal serum from different animal species. This reaction is due to a specific binding between the surface of the bacteria and fibrin/fibrinogen.

It has now been found that receptors like those being present in staphylococci also exist in other microorganisms. Frequence studies on e.g. strains of staphylococci and streptococci isolated from wound infections and other types of infections show that the ability of binding e.g. fibronectin is contributed to the virulence of the microorganisms. In infections caused e.g. by *Staphylococcus aureus* and coagulase negative staphylococci this binding ability contributes to the virulence by making an initial tissue colorization possible.

Surprisingly it has now been found that proteins or fragments or residues thereof, optionally bound to a carrier, are suitable means for removing microorganisms from tissue. The present invention thus concerns means for removing microorganisms from tissue, such as mucous membranes, skin and wound tissue, which means comprises at least one protein or a fragment or residue thereof which can be bound to the microorganisms, and optionally a carrier to which the protein or fragment or residue thereof is bound.

Suitable proteins to be used in accordance with the invention are fibrinogen, fibronectin, an immunoglobulin, albumin, haptoglobin, β-2-microglobulin, collagen, laminin, entactin or chondronectin. Further, fragments or residues of these proteins are also suitable. These fragments or residues can be peptides having a molecular weight of $5 \times 10^2 - 10^5$, preferably $5 \times 10^2 - 5 \times 10^4$.

Suitable carriers to be used in accordance with the invention are polymer materials, such as agarose or a derivative thereof, starch or a derivative thereof, cellulose or a derivative thereof, dextran or a derivative thereof, or an alginate. Further, a fiber material being a part of absorption products, such as a dressing or a tampon, is also suitable.

Proteins or fragment(s) or residue(s) thereof can be bound to the carrier in a manner known per se, and that through a covalent bond via the carbohydrate part, the primary amino groups, the sulfhydryl or the carboxy groups in the protein, e.g. by means of divinyl sulfone, epichlorohydrin, carbodiimide, by means of transamination or via cyanobromide bridges, or by biospecific interactions known per se, such as the binding of fibronectin to gelatin, the binding of glycoproteins to lectin or the binding of antigens to antibodies.

The proteins or fragments or residues thereof can also be absorbed directly on a carrier.

The present invention is further illustrated in the following examples:

Example 1

Skin areas on human loin was washed with a physiological saline solution. Then about $10^7$ and $10^9$ *Staphylococcus aureus* (strain Newman) were applied on several skin areas. A gel of Sepharose ®4B, to which fibronectin had been bound, was applied to the skin areas on which strain Newman had been applied, and that in 2–3 mm thick layers. The fibronectin had been bound to a cyanobromide activated gel of Sepharose ®4B by incubating 10 mg of fibronectin per ml cyanobromide activated gel for 2 h at room temperature and under a gentle stirring. The reaction was terminated by adding 1M glycine solution to the reaction mixture, whereafter the incubation was continued for further 30 minutes. Before use the gel was thoroughly washed. Pure Sepharose ®4B was used as control gel and applied in the same manner on the other skin areas on which strain Newman had been applied. All skin areas were dried with a fan (cold air). After 20–30 minutes test gel as well as control gel were removed by a sterile scalpel. Thereafter fresh material of both gels were applied and the procedure was repeated until totally 3 treatments had been carried out, and that during a period of time of about 2 h.

After the completed procedure cultivation shows that strain Newman had been removed almost completely (only single colonies of bacteria were observed) whereas cultivations from skin areas where control gel had been applied only showed a small decrease in bacteria number.

Example 2

Example 1 was repeated, but instead of strain Newman *Staphylococcus aureus* (strain V 8) was used. The same type of control gel was also used. The cultivation check after the completed treatment showed a growth of strain V 8 that was considerably larger than that for strain Newman of example 1.

Example 3

Example 1 was repeated, and instead of fibronectin, fibrinogen was used. The binding of fibrinogen to the gel of Sepharose ®4B was established in the same manner as for fibronectin in example 1. A gel of pure Sepharose ®4B was used as a control gel.

Cultivation after the completed procedure shows that strain V 8 had been almost completely removed (only single colonies were observed) while cultivations from skin areas being treated with control gel only showed a small decrease in bacteria number.

These examples show that strain Newman has a fibronectin receptor whereas strain V 8 is bound very weakly to fibronectin, but has a fibrinogen receptor. It is further evident that a strain having a Fn receptor is removed specifically.

Examples 4–19

Example 1 was repeated using *Staphylococcus aureus*, strain SA 113 and strain Cowan 1, and group A streptococci, strain H 15757 and strain 11270.

The proteins used were albumin, immunoglobulin G, fibrinogen and fibronectin, respectively, and there were bound to a gel of Sepharose 4B in the same way as was fibronectin in example 1. In all the examples gel of pure Sepharose ®4B was used as a control gel.

The procedure described in example 1 was carried out and subsequent cultivation showed the hereinafter given results for the different organisms and proteins, respectively.

When fibronectin was used *Staphylococcus aureus* (Strain SA 113) was cultivation negative (only single colonies of bacteria were observed), whereas positive cultivation results of this strain were obtained when albumin, immunoglobulin G and fibrinogen, respectively, were used.

*Staphylococcus aureus* (strain Cowan 1) was cultivation negative when immunoglobulin G, fibrinogen and fibronectin, respectively, was used, whereas positive cultivation results of this strain were obtained when albumin was used.

Group A streptococcus (strain H 15757) was cultivation negative when albumin and fibronectin, respectively, were used, whereas positive cultivation results of this strain were obtained when immunoglobulin G and fibrinogen, respectively, were used.

Group A streptococcus (strain 11270) was cultivation negative when fibrinogen was used, whereas positive cultivation results of this strain were obtained when albumin, immunoglobulin G and fibronectin, respectively, were used.

Cultures from skin areas where control gel had been applied gave in all cases positive cultivation results.

Example 20

Hospital personnel with a recognized colonization of antibiotic resistent *Staphylococcus aureus* were divided into two groups, each of the same size (test and control group, respectively). Samples from all persons in the two groups exhibited repeated positive cultivation results. The test group was treated with cotton swabs, that had been dipped in a fibronectin solution, which swabs were plugged in the nostrils and kept there for a couple of hours, whereafter they were exchanged with fresh swabs, also being dipped in the fibronectin solution. The procedure was repeated so that the treatment was carried out totally 3 times. The control group was treated in the same way, but unprepared swabs were used.

Samples from the persons in the control group after the completion procedure were cultivation positive, whereas samples from the persons in the test group were completely negative.

EXAMPLE 21

Mice (20-30 g, CBA strain) were shaved and subjected to a second or third degree burn according to an international standard on an area of 1×1 cm (ethanol flame, 2 minutes). *Staphylococcus aureus* (strain Cowan 1) was used as microorganism in this example. Suspensions of 10 microorganisms per ml saline solution (phosphate buffered) was prepared and all mice were painted with 0.5 ml of the suspension on the burnt area. The mice were then divided into a test and a control group. The mice of the test group were treated with fibronectin bounded to a gel of Sepharose ®4B whereas the mice of the control group were treated with pure Sepharose ®4B. The treatment was carried out so that the gel was applied to the burnt area in a confluent layer being about 2-3 mm thick. After removing of one layer by scraping with a scalpel a fresh layer was applied, and the treatment was repeated until totally three layers of gel had been applied and removed. Then samples were taken from the burnt area, which samples were cultivated.

Samples from mice in the test group were cultivation negative (i.e. 1-3 colonies) after 1 day. Samples from mice in the control group were cultivation positive (more than 3 colonies up to confluent growth) still after 3 days.

Example 22

The same type of mice as those of example 21 was used. Instead of *S. aureus Staphylococcus capitis*, LK 499 was used, but besides that the procedure of example 21 was repeated.

Samples from mice in the test group were cultivation positive on day 2, whereas samples from mice in the control group were cultivation positive still on day 4.

Example 23

The same type of mice as those of example 21 was used. Instead of *S. auerues Staphylococcus haemolyticus* was used, but besides that the procedure of example 21 was repeated.

Samples from mice in the test as well as control group were cultivation positive after day 3.

Example 24

The same procedure and strain as in examples 21 were used and also the same type of mice, but the mice in the test group were treated with fibrinogen bound to a gel of Sepharose ®4B.

Samples from mice in the test group were cultivation negative on day 2, whereas samples from mice in the control group were cultivation positive on day 4.

Example 25

The same procedure and strain as in example 22 were used and also the same type of mice, but the mice of the test group were treated with fibrinogen bound to a gel of Sepharose ®4B.

Samples from mice in the test as well as the control group were cultivation positive after 4 days.

Example 26

The same procedure and strain as in example 23 were used and also the same type of mice, but the mice in the test group were treated with fibrinogen bound to a gel of Sepharose ®4B.

Samples from mice in the test as well as the control group were cultivation positive after 4 days.

From the examples is evident that different microorganisms bind to different proteins. The bindings shown between the microorganisms and protein, respectively, have been confirmed by in vitro experiments. These have been carried out by incubating respectively microorganism with respectively protein, the latter being labelled with radioactive iodine. After completed incubation the amount of radioactively labelled proteins bound to respective microorganism was measured. In those cases where the microorganisms have been removed by the treatment with a protein (cultivation negative samples), in vitro experiments have proved that respective microorganisms has been bound to the radioactively labelled protein, whereas in those cases where the microorganisms have not been removed (cultivation positive samples) after the treatment with a protein, in vitro experiments have proved that there is no bond between the corresponding microorganism and radioactively labelled protein.

The proteins can also be bound to fiber materials being a part of an absorption product, such as dressings or tampons in order to remove microorganisms from wound or other tissue. Dressings, to which the proteins are bound are suitable for the treatment of wounds. Tampons to which a protein has been bound can e.g. be used in surgery for absorbing from surgical wounds, or as catamenial tampons, where they can be used for removing the microorganisms being the cause of the so called tampon disease.

The means of the present invention can also be used for removing microorganisms in wound hollows, who e.g. are the result of an opening of abscesses, such as anal abscesses, in which case the means preferably is bound to a dressing having the shape of the wound hollow in order to fill this up and to inhibit the closing of the abscess. Such a dressing material can e.g. be in fiber or granular form in an absorption material enclosed in a hydrofobic material. The protein can further be in the form of a rinsing solution for removing of microorganisms in local infections.

We claim:

1. A method for treating a microorganism infection on a wound comprising applying to microorganisms on the wound an effective amount of a protein or fragment or residue thereof to bind to microorganisms, said protein selected from the group consisting of fibronectin, fibrinogen, collagen, laminin and chondronectin, and removing the protein or fragment or residue thereof which is bound to the microorganism from the wound.

2. The method according to claim 1 wherein said protein is bound to a carrier.

3. The method according to claim 1 wherein said protein is fibronectin.

4. The method according to claim 1 wherein said protein is fibrinogen.

5. The method according to claim 1 wherein said protein is collagen.

6. The method according to claim 1 wherein said protein is laminin.

7. The method according to claim 1 wherein said protein is chondronectin.

8. The method according to claim 2 wherein said protein comprises a fibrous material.

9. The method according to claim 8 wherein the fibrous material is part of a dressing.

10. The method according to claim 8 wherein the fibrous material is part of a tampon.

* * * * *